United States Patent [19]

Stacpoole et al.

[11] Patent Number: 5,643,951

[45] Date of Patent: Jul. 1, 1997

[54] COMPOSITIONS COMPRISING CARBONATE/BICARBONATE BUFFERED DICHLOROACETIC ACID AND METHODS FOR TREATMENT OF METABOLIC AND CARDIOVASCULAR DISORDERS

[76] Inventors: Peter W. Stacpoole, 6205 NW. 143rd St., Gainesville, Fla. 32606; Robert M. Bersin, 2005 Cortelyou Rd., Charlotte, N.C. 28211

[21] Appl. No.: 465,608

[22] Filed: Jun. 5, 1995

Related U.S. Application Data

[63] Continuation of Ser. No. 945,374, Sep. 16, 1992, abandoned.
[51] Int. Cl.$^6$ .................. A61K 31/19; A61K 31/075
[52] U.S. Cl. .................. 514/557; 514/715; 514/717; 514/824; 514/866
[58] Field of Search .................. 514/557, 715, 514/717, 824, 866

[56] References Cited

PUBLICATIONS

CA 108: 143192y, Dimlich et al., 1988.
Bersin et al., "Improved Hemodynamic Function During Hypoxia with Carbicarb*, A New Agent for the Management of Acidosis, Circulation"77(1), p. 227–233, 1988.

CA103:171834z, Graf et al., 1985.

*Primary Examiner*—Kimberly Jordan
*Attorney, Agent, or Firm*—Dennis P. Clarke; Kerkam, Stowell, Kondracki & Clarke, P.C.

[57] ABSTRACT

Methods for the treatment of metabolic and/or cardiovascular disorders comprising administering to a human in need thereof a therapeutically effective amount of a composition comprising dichloroacetic acid or a pharmaceutically acceptable salt or derivative thereof and a pharmaceutically acceptable mixture of carbonate and bicarbonate ions, the weight ratio of dichloroacetic acid, derivative or salt thereof to the mixture of carbonate and bicarbonate ions being in the range of from about 100:1 to about 0.01:1. Also disclosed are pharmaceutical compositions in unit dosage form adapted for administration to a human for the treatment of metabolic and/or cardiovascular disorders comprising a therapeutically effective amount of a composition comprising dichloroacetic acid or a pharmaceutically acceptable salt or derivative thereof and a pharmaceutically acceptable mixture of carbonate and bicarbonate ions, the weight ratio of dichloroacetic acid, derivative or salt thereof to the mixture of carbonate and bicarbonate ions being in the range of from about 100:1 to about 0.01:1; and a pharmaceutically acceptable carrier therefor.

10 Claims, No Drawings

COMPOSITIONS COMPRISING CARBONATE/BICARBONATE BUFFERED DICHLOROACETIC ACID AND METHODS FOR TREATMENT OF METABOLIC AND CARDIOVASCULAR DISORDERS

This is a continuation of application Ser. No. 07/945,374 filed Sep. 16, 1992, now abandoned.

BACKGROUND OF THE INVENTION

1. Field of the Invention

The present invention relates to pharmaceutical compositions and methods for the treatment of metabolic and cardiovascular disorders and to certain dichloroacetate derivatives as the active ingredients therein.

2. Discussion of the Prior Art

The pharmacologic and therapeutic properties of salts of dichloroacetic acid (DCA) have been extensively studied over the last several years [Stacpoole, Metabolism, Vol. 38, No. 11, pages 1124–1144 (1989)].

Researchers have found that DCA stimulates glucose uptake and utilization by peripheral tissues [Stacpoole et al, Metabolism, Vol. 19:71 (1970); McAllister et al, Biochem. J., Vol. 134:1067 (1973); Diamond et al, Diabetes, Vol. 31:326 (1982)] and inhibits hepatic glucose production [Stacpoole, Metabolism, Vol. 26:107 (1977); Demangre et al, Biochem. J., Vol. 172:91 (1978); Diamond et al, Metabolism, Vol. 30:880 (1981)]. It has also been found to decrease blood glucose levels in patients with diabetes mellitus [Stacpoole et al, N. Eng. J. Med., Vol. 298:526 (1978)]. DCA also stimulates lactate oxidation in animal tissue and significantly decreases lactic acid levels and overall morbidity in patients with lactic acidosis [Stacpoole et al, N. Eng. J. Med., Vol. 309:390 (1983); Blackshear et al, Diabetes Care, Vol. 52391 (1982)]. In addition, DCA reduces circulating triglyceride and cholesterol concentrations in obese [Felts et al, Diabetes, Vol. 25 (suppl.):363 (1976)] and diabetic [Hayet et al, Metabolism, vol. 29:120 (1980); Riles et al, Diabetes, Vol. 28:852 (1979)] animals. DCA also markedly decreases blood cholesterol levels in patients with various forms of hyperlipidemia [Stacpoole et al, N. Eng. J. Med., Vol. 298:526 (1978); Moore et al, Atherosclerosis, Vol. 33:285 (1979)].

The efficacy of DCA for the treatment of metabolic disorders, however, is compromised by the fact that DCA is toxic to lower animals and humans, particularly upon chronic administration. It has been reported that a human patient who received DCA for about four months developed a mild polyneuropathy that resolved when treatment stopped [Moore et al, ibid]. Chronic administration of DCA to lower animals in doses exceeding those used clinically also induces a reversible peripheral neuropathy, changes in testicular morphology and lenticular opacities [Stacpoole, N. Eng. J. Med., Vol. 300:372 (1979)].

DCA is known to oxidize in vivo to glyoxalate and subsequently to oxalate [Demangre et al, Biochem. Biophys. Res. Comm., Vol. 8521180 (1978); Harris et al, Arch. Biochem. Biophys., Vol. 189:364 (1978) and Currey et al, Clin. Pharmacol. Ther., Vol. 37:894 (1985)]. Oxalate is a known neurotoxin [Bilbao et al, Can. J. Neurol. Sci., Vol. 3:63 (1976)] and cataract inducing chemical [Fielder et al, Br. J. Ophthal., Vol. 64:782 (1980)], and may be at least partly responsible for the neuropathic changes associated with the chronic administration of DCA.

The drug also improves cardiac output and left ventricular mechanical efficiency under conditions of myocardial ischemia or failure, probably by facilitating myocardial metabolism of carbohydrate and lactate as opposed to fat. DCA may also enhance regional lactate removal and restoration of brain function in experimental stages of cerebral ischemia [Stacpoole, Metabolism, ibid].

DCA appears to inhibit its own metabolism, which may influence the duration of its pharmacologic actions and lead to toxicity. DCA can cause a reversible peripheral neuropathy that may be related to thiamine deficiency and may be ameliorated or prevented with thiamine supplementation [Stacpoole, Metabolism, ibid].

Carbicarb™ is a substantially equimolar mixture of sodium carbonate ($Na_2CO_3$) and sodium bicarbonate ($NaHCO_3$) which buffers solutions thereof to bicarbonate ions without a net generation of $CO_2$. The mixture has been employed in humans and animals to restore normal systemic (blood) and/or intracellular pH and acid-base status which results in an improvement in the metabolism and function of cells, tissues and organisms [Filley et al, Trans. Am. Clin. Clinatol Assoc., vol. 96, page 141 (1934); Whalen et al, Clin. Res., Vol. 36, page 374A (1988); and Betsin et al, Circulation, Vol. 77, page 227 (1988)].

It is an object of the present invention to provide novel compositions and methods for the safe and effective treatment of certain metabolic and/or cardiovascular disorders which synergistically combine the therapeutic properties of Carbicarb™ or similar carbonate/bicarbonate buffering systems and DCA.

SUMMARY OF THE INVENTION

The foregoing and other objects are realized by the present invention, embodiments of which are methods for the treatment of metabolic and/or cardiovascular disorders comprising administering to a human in need thereof a therapeutically effective amount of an aqueous composition comprising dichloroacetic acid or a pharmaceutically acceptable salt or derivative thereof and a pharmaceutically acceptable mixture of carbonate and bicarbonate ions, the weight ratio of dichloroacetic acid, derivative or salt thereof to said mixture of carbonate and bicarbonate ions being in the range of from about 100:1 to about 0.01:1.

Other embodiments of the invention include pharmaceutical compositions in unit dosage form adapted for administration to a human for the treatment of metabolic and/or cardiovascular disorders comprising a therapeutically effective amount of a composition comprising dichloroacetic acid or a pharmaceutically acceptable salt or derivative thereof and a pharmaceutically acceptable, substantially equimolar mixture of carbonate ions and bicarbonate ions, the weight ratio of dichloroacetic acid, derivative or salt thereof to said mixture of carbonate and bicarbonate ions being in the range of from about 100:1 to about 0.01:1; and a pharmaceutically acceptable carrier therefor.

DETAILED DESCRIPTION OF THE INVENTION

The present invention is predicated on the discovery that combinations of DCA and mixtures of carbonates and bicarbonates in certain ratios synergistically enhance the therapeutic activities of each agent when administered in therapeutically effective dosages to humans in need of treatment for metabolic and/or cardiovascular disorders.

This mutually synergistic effect enables the administration of smaller dosages of each agent than when each is administered separately, thereby ameliorating the toxicity of each agent to the patient.

While it is in no way intended to limit the invention by the soundness or accuracy of any theories set forth herein to explain the nature of the invention, it is postulated that the combination of DCA and the carbonate/bicarbonate mixture enhances the effect of each on systemic and intracellular pH and thereby improves the energy metabolism and function of tissues.

DCA would promote aerobic oxidation of lactate and generate by this means increased bicarbonate ions (as a buffer for cells) and increase levels of high energy metabolites, such as ATP and creatine phosphate. The improvement in acid-base and energy status caused by DCA and the carbonate/bicarbonate mixture would, in turn, increase the functional capacity of tissues such as the heart, leading to improved mechanical function and efficiency and better perfusion of tissues by the blood.

It will be understood by those skilled in the art that the terms "carbonate/bicarbonate" and "mixture of carbonate and bicarbonate ions" are intended to include a mixture of carbonate and bicarbonate salt, e.g., sodium carbonate and sodium bicarbonate, which is therapeutically effective for the treatment of metabolic and/or cardiovascular disorders such as, for example, Carbicarb™, an agent well known in the art as evidenced by the references to Filley et al, Shapiro et al and Betsin et al, supra, and which comprises a mixture containing an equimolar ratio of sodium carbonate to sodium bicarbonate.

It will be further understood by those skilled in the art that the term "DCA" is intended to include dichloroacetic acid, salts thereof with pharmaceutically acceptable cations, e.g., sodium, potassium, diisopropylammonium, and derivatives thereof which possess the therapeutic properties and activities of dichloroacetic acid such as the compounds described in U.S. Pat. Nos. 4,801,497 and 4,558,050, the entire disclosures of which are incorporated herein by reference.

It is preferred to form the composition of the invention by admixing DCA with a suitable carbonate, e.g., sodium carbonate in solution. Free hydrogen ion liberated in solution by the DCA is buffered by the carbonate ions to form free bicarbonate ions. Where the amount of free hydrogen ion liberated is an amount sufficient to result in buffering of half of the carbonate to bicarbonate, the result will be a mixture of DCA and an equimolar mixture of sodium carbonate and sodium bicarbonate, i.e., a mixture of DCA and Carbicarb™.

It has been found that the methods and compositions of the invention are suitable for the treatment of a wide variety of metabolic disorders, e.g., lactic acidosis, diabetes mellitus, hyperlipidemia, catabolic states and neurologic disorders associated with abnormal carbohydrate, lactic acid or lipid metabolism.

Cardiovascular disorders for which the compositions and methods of the invention are useful for treating include heart failure, myocardial ischemia, myocardial infarction, cardiac arrythmia, cerebrovascular insufficiency or stroke.

It will be understood by those skilled in the art that the compositions and methods of the invention are applicable for the treatment of any metabolic and/or cardiovascular disorder or disease against which DCA or carbonate/bicarbonate alone is effective.

The compositions and methods of the invention are particularly adapted for the treatment of lactic acidosis and myocardial dysfunction.

The above dichloroacetate derivatives may be formulated with pharmaceutically acceptable carriers adapted for oral administration (i.e., tablet, capsule or pill) and administered orally. The active agent may also be compounded for parenteral or transdermal administration. The active ingredient may be admixed or compounded with any conventional pharmaceutically acceptable carrier. It will be understood by those skilled in the art that any mode of administration, vehicle or carrier heretofore employed for the administration of DCA alone may be utilized for preparation and administration of the pharmaceutical compositions of the present invention. Illustrative of such methods, vehicles and carriers are those described by Stacpoole et al [N. Eng. J. Med., Vol. 309:390 (1983) and N. Eng. J. Med., Vol. 298:526 (1978)]. Those skilled in the art, having been exposed to the principles of the invention, will experience no difficulty in determining suitable and appropriate vehicles, excipients and carriers or in compounding the active ingredients therewith to form the pharmaceutical compositions of the invention.

While it is possible for the derivatives to be administered as the raw substances, it is preferable, in view of their potency, to present them as a pharmaceutical formulation. The formulations, both for veterinary and for human use, of the present invention comprise a derivative together with one or more acceptable carriers therefor and optionally other therapeutic ingredients. The carrier(s) must be "acceptable" in the sense of being compatible with the other ingredients of the formulation and not deleterious to the recipient thereof. Desirably, the formulations should not include oxidizing agents and other substances with which the derivatives are known to be incompatible. The formulations may conveniently be presented in unit dosage form and may be prepared by any of the methods well known in the art of pharmacy. All methods include the step of bringing into association the derivative with the carrier which constitutes one or more accessory ingredients. In general, the formulations are prepared by uniformly and intimately bringing into association the derivative with the carrier(s) and then, if necessary, dividing the product into unit dosages thereof.

Formulations suitable for parenteral administration conveniently comprise sterile aqueous preparations of the derivatives which are preferably isotonic with the blood of the recipient. Such formulations may be conveniently prepared by admixing solid derivatives with water to produce a solution or suspension which is filled into a sterile container and sealed against bacterial contamination. Preferably, sterile materials are used under aseptic manufacturing conditions to avoid the need for terminal sterilization.

Such formulations may optionally contain one or more additional ingredients among which may be mentioned preservatives, such as methyl hydroxybenzoate, chlorocresol, metacresol, phenol and benzalkonium chloride. Such materials are of special value when the formulations are presented in multi-dose containers.

Buffers may also be included to provide a suitable pH value for the formulation. Acceptable materials for such buffers include sodium phosphate and acetate. Sodium chloride or glycerin may be used to render a formulation isotonic with the blood. If desired, the formulations may be filled into the containers under an inert atmosphere such as nitrogen or may contain an antioxidant, and are conveniently presented in unit dose or multi-dose form, e.g., in a sealed ampoule.

The therapeutically effective amount of DCA and carbonate/bicarbonate to be included in the pharmaceutical composition of the invention depends, in each case, upon several factors, e.g., the type, size and condition of the animal, the disorder to be treated, the intended mode of administration, the capacity of the animal to incorporate the intended dosage form, etc. Generally, amounts of DCA and carbonate/bicarbonate are included in each dosage form to provide amounts of DCA and carbonate/bicarbonate employed in conventional pharmaceutical compositions containing the agents alone.

When administered orally for the treatment of metabolic disorders, the compositions of the invention are formulated such that the dose of DCA is in the range of from about 1 to about 100 mg/kg, body weight, and preferably from about 5 to about 50 mg/kg, and the dose of carbonate/bicarbonate is in the range of from about 0.2 to about 10 mEq/kg, body weight, and preferably from about I to about 5 mEq/kg, body weight.

When administered parenterally for the treatment of metabolic disorders, the composition of the invention is formulated such that the dose of DCA is in the range of from about 1 to about 200 mg/kg, body weight, and preferably from about 10 to about 100 mg/kg, and the dose of carbonate/bicarbonate is in the range of from about 0.2 to about 10 mEq/kg, body weight, and preferably from about 1 to about 5 mEg/kg, body weight.

When administered orally for the treatment of cardiovascular disorders, the compositions of the invention are formulated such that the dose of DCA is in the range of from about 1 to about 100 mg/kg, body weight, and preferably from about 5 to about 50 mg/kg, and the dose of carbonate/bicarbonate is in the range of from about 0.2 to about 10 mEq/kg, body weight, and preferably from about I to about 5 mEq/kg, body weight.

When administered parenterally for the treatment of cardiovascular disorders, the composition of the invention is formulated such that the dose of DCA is in the range of from about 1 to about 200 mg/kg, body weight, and preferably from about 10 to about 100 mg/kg, and the dose of carbonate/bicarbonate is in the range of from about 0.2 to about 10 mEq/kg, body weight, and preferably from about 1 to about 5 mEq/kg, body weight.

We claim:

1. A method for the treatment of a metabolic disorder comprising administering to a human in need thereof a therapeutically effective amount of an aqueous composition comprising dichloroacetic acid or a pharmaceutically acceptable salt or derivative thereof and a pharmaceutically acceptable mixture of carbonate and bicarbonate ions, the weight ratio of dichloroacetic acid or salt thereof to said mixture of carbonate and bicarbonate ions being in the range of from about 100:1 to about 0.01:1.

2. A method according to claim 1, wherein said metabolic disorder is lactic acidosis, diabetes mellitus, hyperlipidemia, a catabolic state or a neurological disorder associated with abnormal carbohydrate, lactic acid or lipid metabolism.

3. A method according to claim 1, wherein said composition is administered orally such that the dose of said dichloroacetic acid, derivative or salt thereof is in the range of from about 1 mg/kg to about 100 mg/kg, body weight, and the dose of said mixture of carbonate and bicarbonate ions is in the range of from about 0.2 mEq/kg to about 10 mEq/kg, body weight.

4. A method according to claim 1, wherein said composition is administered orally such that the dose of said dichloroacetic acid, derivative or salt thereof is in the range of from about 5 mg/kg to about 50 mg/kg, body weight, and the dose of said mixture of carbonate and bicarbonate ions is in the range of from about 1 mEq/kg to about 5 mEq/kg, body weight.

5. A method according to claim 1, wherein said composition is administered parenterally such that the dose of said dichloroacetic acid, derivative or salt thereof is in the range of from about 1 mg/kg to about 200 mg/kg, body weight, and the dose of said mixture of carbonate and bicarbonate ions is in the range of from about 0.2 mEq/kg to about 10 mEq/kg, body weight.

6. A method according to claim 1, wherein said composition is administered parenterally such that the dose of said dichloroacetic acid, derivative or salt thereof is in the range of from about 10 mg/kg to about 100 mg/kg, body weight, and the dose of said mixture of carbonate and bicarbonate ions is in the range of from about 1 mEq/kg to about 5 mEq/kg, body weight.

7. A method according to claim 1 wherein said mixture of carbonate and bicarbonate ions contains a substantially equimolar amount of carbonate and bicarbonate ions.

8. A pharmaceutical composition in unit dosage form adapted for administration to a human for the treatment of a metabolic disorder comprising a therapeutically effective amount of a composition comprising dichloroacetic acid or a pharmaceutically acceptable salt or derivative thereof and a pharmaceutically acceptable mixture of carbonate and bicarbonate ions, the weight ratio of dichloroacetic acid or salt thereof to said mixture of carbonate and bicarbonate ions being in the range of from about 100:1 to about 0.01:1; and a pharmaceutically acceptable carrier therefor.

9. A composition according to claim 8, wherein said metabolic disorder is lactic acidosis, diabetes mellitus, hyperlipidemia, a catabolic state or a neurologic disorder associated with abnormal carbohydrate, lactic acid or lipid metabolism.

10. A pharmaceutical composition according to claim 8 wherein said mixture of carbonate and bicarbonate ions contains a substantially equimolar amount of carbonate and bicarbonate ions.

* * * * *